United States Patent [19]

Fong et al.

[11] Patent Number: 4,734,473

[45] Date of Patent: Mar. 29, 1988

[54] WATER-SOLUBLE CATIONIC QUATERNARY AMMONIUM MONOMERS

[75] Inventors: Dodd W. Fong, Naperville; David J. Kowalski, LaGrange Park, both of Ill.

[73] Assignee: Nalco Chemical Company, Naperville, Ill.

[21] Appl. No.: 937,262

[22] Filed: Dec. 3, 1986

Related U.S. Application Data

[62] Division of Ser. No. 621,338, Jun. 15, 1984, Pat. No. 4,656,277.

[51] Int. Cl.$^4$ .................... C08F 26/12; C08F 126/08
[52] U.S. Cl. .................................. 526/263; 525/326.7
[58] Field of Search ...................... 526/263; 525/326.7

[56] References Cited

U.S. PATENT DOCUMENTS 2,843,573  5/1956  Melamed ........................... 526/291
3,284,393  11/1966  Vanderhoff et al. ............... 526/263

OTHER PUBLICATIONS

79 CA 151603f, German Offen., 2,312,708, Miyazako, et al.
80 CA 151111g, Japanese Kokai, 73/85222, Miyazako, et al.
85 CA 51750g, German Offen., 2,546,241, Ferruti, et al.
85 CA 51751h, German Offen., 2,546,240, Ferruti, et al.
87 CA 85501h, German Offen., 2,550,547, Naarmann, et al.
88 CA 89716a, German Offen., 2,623,838, Pohlemann, et al.
94 CA 90348n, U.S. Pat. No., 4,228,152, Ferruti, et al.
88 CA 113310m, Japanese Kokai 77/102722, Chujo, et al.

Primary Examiner—John Kight
Assistant Examiner—M. L. Moore
Attorney, Agent, or Firm—John G. Premo; Anthony L. Cupoli; Donald G. Epple

[57] ABSTRACT

The methyl chloride or dimethyl sulfate quaternary ammonium salt of 1-methacryloyl-4-methyl piperazine.

6 Claims, No Drawings

WATER-SOLUBLE CATIONIC QUATERNARY AMMONIUM MONOMERS

The present application is a division of U.S. Ser. No. 621,338, filed June 15, 1984, now U.S. Pat. No. 4,656,277.

THE INVENTION

The present invention is concerned with the methyl chloride or dimethyl sulfate quaternary ammonium salts of 1-methacryloyl-4-methyl piperazine. It is also directed to the homopolymers as well as the acrylamide copolymers of these novel monomers.

The starting vinyl monomer used to prepare the ammonium salts is 1-methacryloyl-4-methyl piperazine. This monomer is reacted with appropriate amounts of methyl chloride or dimethyl sulfate to produce the compounds of the invention. To prepare the starting materials, acryloyl chloride is reacted with N-methyl-piperazine.

The monomers may be either homopolymerized or may be copolymerized with other vinyl addition monomers capable of being polymerized with the monomers of this invention. The resultant homopolymers will be water-soluble. Copolymers may be either water-soluble or water insoluble. A particularly useful water-soluble copolymer may be prepared by polymerizing the monomers of this invention with acrylamide. Homopolymers and copolymers of the monomers of this invention with acrylamide have a variety of industrial uses such as, for example flocculants and dewatering agents.

The monomers of this invention may be copolymerized with either water-soluble or water-insoluble vinyl addition monomers having suitable reactivity ratios. The co-monomers may be either nonionic, cationic, or anionic. Examples of suitable non-ionic monomers include: acrylamide, methacrylamide, acrylonitrile, vinyl acetate, lower alkyl acrylates, lower alkyl methacrylates, lower alkyl ethacrylates, styrene, etc. Examples of suitable anionic co-monomers useful in this invention include: acrylic acid, methacrylic acid, itaconic acid, maleic anhydride, acrylamidomethylpropanesulfonic acid, etc. Examples of suitable cationic monomers which may be useful in this invention include: dimethyl-aminoethylacrylate, quaternary salts of dimethylamino-ethylacrylate, dimethylaminoethylmethacrylate, dimethylaminoethylmethacrylate quaternaries, diallyldimethylammonium chloride, methacrylamidopropyltrimethylammonium chloride, N-vinyl pyrrolidone, vinyl pyridine, N,N-dimethylaminomethylacrylamide, N,N-dimethylaminomethylmethacrylamide, N,N-dimethylaminomethylacrylamide quaternaries, etc.

All that is important is that the co-monomer be capable of polymerizing, or have suitable reactivity ratios, with the monomers of this invention. Generally when copolymerized such copolymers will contain from 1-99 mole percent, preferably 1-70 mole percent and most preferably 2-50 mole percent of the comonomer or comonomers employed.

The polymers and copolymers of the invention can be prepared either using conventional solution polymerization techniques or the so-called inverse emulsion polymerization method which utilizes polymerization of water-soluble vinyl monomers in the form of water-in-oil emulsions. This technique is described in Vanderhoff, U.S. Pat. No. 3,284,393, the disclosure of which is incorporated herein by reference.

EXAMPLES

To illustrate the invention, the following are given by way of example:

Example 1

Synthesis of 1-methacrylol-4-methyl piperazine

Methacryloyl chloride (102 g) in methylene chloride (100 ml) was added into a methylene chloride (450 ml) solution of N-methyl piperazine (86 g) over a period of one hour. The reaction temperature was kept below 25° C. with cooling. After the addition was completed, the reaction mixture was stirred at ambient temperature for two hours. Then, sodium carbonate (46 g) in water (215 g) was added into the reaction mixture with stirring. A crude product of 1-methacryloyl-4-methyl piperazine (100 g) was recovered from the methylene chloride solution. The product was distilled and the fraction collected at 74°–78° C./5 mm Hg was characterized by I.R. and C13 NMR.

Example 2

Quaternization of 1-methacryloyl-4-methyl piperazine 23.2 g. dimethyl sulfate was added slowly into 30 g. 1-methacryloyl-4-methyl piperazine in 51.8 g. water with cooling so that the reaction temperature was kept below 30° C. After the addition was completed, the reaction mixture was stirred at ambient temperature for two hours. The product was characterized by C13 NMR.

Into a 300 ml Parr bomb was charged 26.6 g. water, 21 g. 1-methacryloyl-4-methyl piperazine, and 10 g. methyl chloride. The valves were closed and the bomb was heated to and maintained at 60° C. for 2½ hours. The product was characterized by C13 NMR.

Example 3

| Water-in-Oil Emulsion Polymerization of Acrylamide and MAMPIPQUAT | |
|---|---|
| Oil Phase: | |
| LOPS | 130.0 g |
| Sorbitan Monooleate | 7.5 g |
| 4 moles EO reacted with Sorbitan Monostearate | 2.5 g |
| Aqueous Phase: | |
| 50% MAMPIP MSQ[1] | 51.25 g |
| 46.4% Acrylamide solution | 246.49 g |
| $H_2O$ | 59.92 g |
| Versene | .05 g |
| Initiator: | |
| 2,2'-Azobisisobutyronitrile | .28 g |

The oil and the aqueous phases (pH 5) were first prepared and the emulsion was obtained by adding the aqueous solution into the LOPS solution with vigorous stirring.

The emulsion was purged with nitrogen for ½ hour and then heated to 45° C. The initiator was added. The reaction was maintained at 45° C. for four hours and at 65° C. for one hour. The reaction was stopped and cooled to room temperature. G.C. analysis of the residual monomer shows the polymerization was 74% complete. IV of the copolymer was 7.0.

The above quaternary ammonium salt monomers may be polymerized either by way of solution or by way of the so-called "water-in-oil" emulsion technique, which process is described in detail in Vanderhoff, U.S. Pat. No. 3,284,393.

Polymers produced using these quaternary ammonium salt monomers are useful as flocculating and dewatering agents.

Having thus described our invention, it is claimed as follows:

1. The homopolymer of the dimethyl sulfate quaternary ammonium salt of 1-methacryloyl-4-methyl piperazine.

2. The homopolymer of the methyl chloride quaternary ammonium salt of 1-methacryloyl-4-methyl piperazine.

3. The copolymer of the dimethyl sulfate quaternary ammonium salt of 1-methacryloyl-4-methyl piperazine with acrylamide, which copolymer contains between 1–99 mole percent of the dimethyl sulfate quaternary ammonium salt of 1-methacryloyl-4-methyl piperazine.

4. The copolymer of the methyl chloride quaternary ammonium salt of 1-methacryloyl-4-methyl piperazine with acrylamide, which copolymer contains between 1–99 mole percent of the methyl chloride quaternary ammonium salt of 1-methacryloyl-4-methyl piperazine.

5. A copolymer of the dimethyl sulfate quaternary ammonium salt of 1-methacryloyl-4-methyl piperazine, with a vinyl addition monomer.

6. A copolymer of the methyl chloride quaternary ammonium salt of 1-methacryloyl-4-methyl piperazine, with a vinyl addition monomer.

* * * * *